United States Patent [19]

Hornbeck

[11] 4,262,424
[45] Apr. 21, 1981

[54] GAUGE FOR DETERMINATION OF SHOULDER BONE ANGLES IN HORSES

[76] Inventor: William W. Hornbeck, Box 461, Mira Loma, Calif. 91752

[21] Appl. No.: 42,562

[22] Filed: May 25, 1979

[51] Int. Cl.³ .......................... G01B 3/56; G01B 5/00
[52] U.S. Cl. .................................... 33/174 D; 33/343
[58] Field of Search ............... 33/1 N, 174 R, 174 D, 33/334, 343, 354, 471

[56] References Cited

U.S. PATENT DOCUMENTS

| | | | |
|---|---|---|---|
| 616,256 | 12/1898 | Platt | 33/343 |
| 751,727 | 2/1904 | Grundeen | 33/343 |
| 946,472 | 1/1910 | Stauffer | 33/343 |
| 3,047,957 | 8/1962 | Conway | 33/343 |

FOREIGN PATENT DOCUMENTS 110514  5/1944  Sweden .................................. 33/471

Primary Examiner—Richard R. Stearns
Attorney, Agent, or Firm—Boniard I. Brown

[57] ABSTRACT

A gauge for the measurement of the shoulder bone angles of horses, as an aid in the proper shoeing of the fore feet, has a reference level and a pointer relatively rotatable about a pivot axis, a concave locating cup concentric with the pivot axis and adapted for positioning over the horse's shoulder point, clamp means releasably securing the pointer and the reference level for selective relative rotation, and protractor means to indicate the relative angle between the pointer and the reference level. The reference level provides determination of the angle between the pointer and a ground plane. The protractor includes a scale and a cooperating needle or index marker, the needle being preferably on the pointer and the scale preferably being on the reference level and concentric with the pivot axis.

8 Claims, 8 Drawing Figures

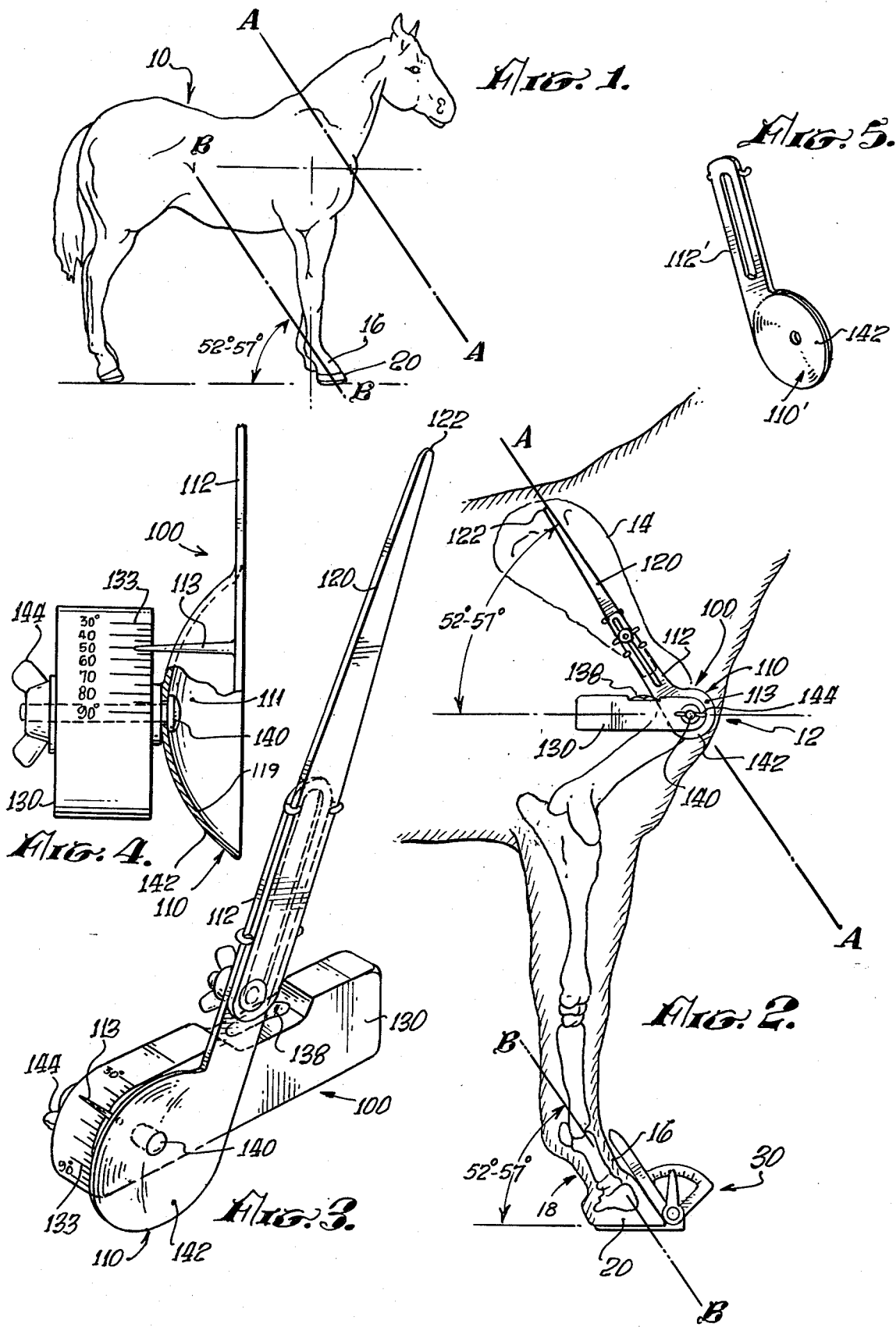

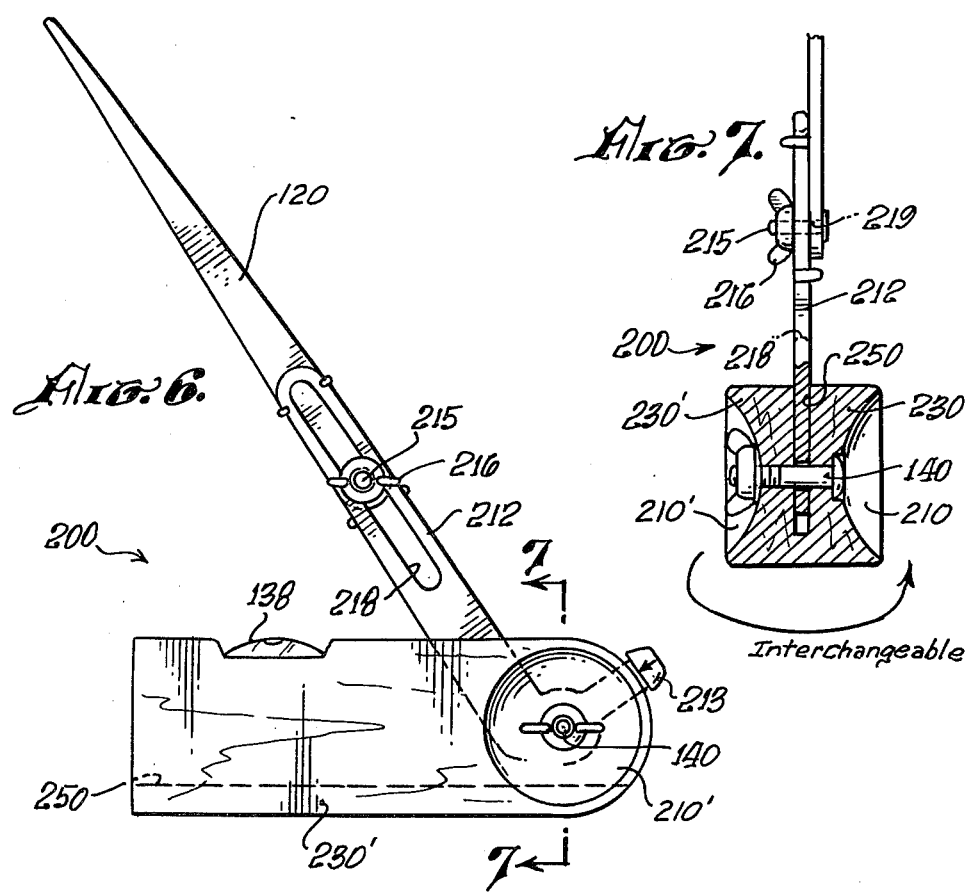
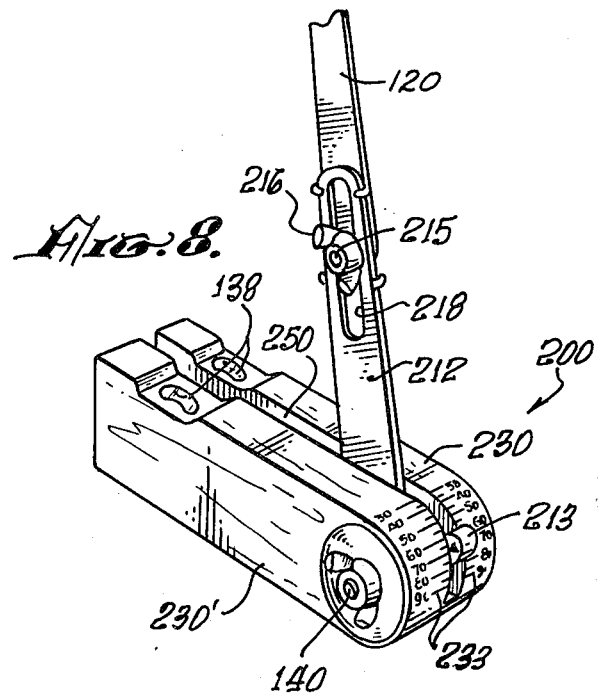

GAUGE FOR DETERMINATION OF SHOULDER BONE ANGLES IN HORSES

BACKGROUND OF THE INVENTION

The present invention relates generally to apparatus for determining the shoulder angles of horses as an aid in proper shoeing, and more particularly such apparatus utilizing cup means for locating the measuring apparatus relative to the shoulder bone knot.

The hoof of the horse is a massive structure of keratinous tissue, corresponding to the nails and claws of other animals, which being without nerve endings and being abradable, is well adapted by process of continous growth and abrasion to be worn into a desirable or optimum configuration with respect to ground contact angle of the hoof for the particular horse, depending upon its weight, conformation, and preferred gait.

It has been known since ancient times that the load carrying and pulling capacity of horses are greatly increased by the provision of additional traction or grip at the hoofground contact. The horse shoe as it is presently known has therefore developed over the centuries, for the purposes of increasing the traction force exerted on the ground by the horses muscular efforts, and to prevent hoof abrasion.

Because horse shoes are not abradable to adapt themselves to appropriate or optimum ground contact angles for particular horses, the horseshoes must be so mounted, for good results, as to be well-adapted to provide the desired ground contact angle in accordance with the conformation, weight and gait of a particular horse. This problem has long been known, and farriers and shoeing smiths have long known that it is preferrable to so shape and mount the shoe that the angle of the forefoot is parallel to the angle of the shoulder bone. Gauges for measuring hoof or forefoot angles have long been known, but determination of correct angles in accordance with shoulder angles, have been dependent upon estimations involving guesswork. Prior shoulder angle measuring devices, such as that described at page 200 of "Horseshoeing Theory and Hoof Care" by Dr. Niles Van Hoosen et al, require considerable skill in the estimation of the run of the shoulder bone and in gauge manipulation.

It is therefore an object of the invention to provide a shoulder-bone angle gauge for use in connection with horseshoeing, which permits quick and accurate determination of the shoulder conformation of a horse.

It is an object of the invention to provide such a gauge when couplings are utilized for location over a shoulder bone joint knot or shoulder point.

SUMMARY OF THE INVENTION

The foregoing objects and other objects and advantages which will become apparent from the detailed description of the preferred embodiment, are attained in a gauge for determining the slope of a shoulder bone of a horse, wherein locating means include at least one concave cup for positioning over the shoulder point, reference level means affixed to the cup, and a pointer rotatable about a pivot axis concentric with the cup preferably, a combination cup and pointer assembly pivotally attached to a reference level on which the protractor is provided.

In utilizing the gauge, the pointer and reference level are released, by releasable clamp means provided, for relative rotation and the cup is positioned over the shoulder bone knot of the horse, the tip being centered on the crest of the horse's withers and held in that position. The reference level assembly is brought into alignment with the horizontal utilizng level means incorporated therein, and the clamp means is tightened. The shoulder angle is read on the protactor on the reference level, and shoes are adapted and mounted to position of the hoofs in correct, corresponding angular relation to the ground.

The cup for receiving the shoulder knot may be defined in the reference level assembly, with the pointer pivotable thereon. The pointer may be adjustable in length to be readily adaptable to the varying shoulder dimensions of horses. In a modified form of the invention, two cups may be provided, facing in opposite directions, thus to facilitate the measurements of both the left and right shoulder points of a horse, this being particularly important with respect to horses having asymmetrical conformations requiring different shoe fittings for the left and right front hooves.

BRIEF DESCRIPTION OF THE ACCOMPANYING DRAWING

FIG. 1 is a side elevational view of a typical horse with indications of preferred shoulder and fore-hoof angles;

FIG. 2 is an enlarged, partial elevational view, showing a horse's shoulder, leg and hoof portions, with a shoulder gauge of the invention in operative arrangement for gauging shoulder bone angle with a hoof gauge measuring parallel alignment of the forefoot with shoulder angle thus determined;

FIG. 3 is an enlarged perspective view of the shoulder angle gauge shown in FIG. 2;

FIG. 4 is a front elevational view of the gauge of FIG. 3;

FIG. 5 is a perspective view of another form of the cup portion of the gauge of FIG. 3, with opposite concavity;

FIG. 6 is an elevational view of another embodiment of the horse shoulder angle gauge of the invention, wherein two locating cups are defined for gauging right and left shoulder bone knots;

FIG. 7 is a sectional elevational view taken at line 7—7 in FIG. 6;

FIG. 8 is a perspective view of the gauge of FIGS. 6 and 7.

DESCRIPTION OF THE PREFERRED EMBODIMENT

Referring to FIGS. 1 and 2, a horse 10 is shown standing at rest with lines A—A and B—B indicating the angles of shoulder bone and the hoof respectively, the horse being shod in the proper manner. It will be noted that the lines A—A and B—B are parallel and, for horses of normal size and conformation, make an angle with the ground of the order of 52–57 degrees. The line A—A extends along shoulder bone 14 of the horse 10 and is centered over a bony knot 12 at the lower shoulder joint, commonly known as the point of the shoulder. The upper end of the line exits the horse's body at a point known as the crest of the withers. These anatomical features are readily identified by all those skilled in the care of horses and define the run of the shoulder bone.

The line B—B may be defined as extending along the axis of the horse's pastern 16, that portion of the foreleg interconnecting hoof 20 with fetlock 18. This line B—B parallels, with a high degree of reliability, the frontal angle of the hoof 20, allowing a hoof gauge 30 of the prior art to be employed in determining the angle between line B—B and the ground plane.

FIG. 2 shows a shoulder angle gauge 100 of the invention measuring the alignment of the line A—A and of the underlying shoulder bone, so as to permit the adjustment of hoof gauge 30 to reflect the proper angle the hoof 20 is to assume to bring the horse's stance into proper balance. The gauge 100 has a cup 110 which is fitted over the shoulder bone knot 12, a pointer 120 aligned with the crest of the withers, and a reference level 130 pivotable on pivot screw 140 to provide a measurement reference parallel with the ground.

FIG. 3 is a perspective, more detailed view of the gauge 100, showing the concave inner surface of the cup 110, the head of pivot screw 140, and wing nut 144 mating therewith to provide releasable securement for selective relative rotation between cup 110 and level 130. A stub portion 112 extends integrally from cup 110, and pointer 120 is mounted thereon for lengthwise positional adjustment by means of the wing nut, screw and slot arrangement shown, appropriate tabs on both the stub portion and on the pointer serving to maintain alignment. The lengthwise adjustment of the pointer provides adjustment for the sizes of particular horses being measured, and assists with the accurate alignment of tip 122 of the pointer 120 with the crest of the animal's withers. A scale needle 113 is affixed near the edge of cup 110 and rotates over a semi-circular reference scale 133 marked on a curved portion of housing 130 which is concentric with the pivot screw 140.

In use, the gauge is applied by placing the cup 110 over the knot of the shoulder bone, thus to provide a fixed reference on the horse's body. The pointer 120 is adjusted relative to the stub 112 so as to place its point 122 into the radial distance of the crest of the withers. The wing nut 144 is loosened to permit the rotation of the level 130 until the bubble in curved indicator glass 138 is centered at the top, indicating the alignment of the level body 130 with the horizontal. Wing nut 144 is tightened to maintain the relative alignment between the level and the pointer, and the gauge is removed for a reading of the shoulder angle, by noting the position of scale needle 113 on the scale 133. The hoof gauge 30 may then be set to the corresponding angle, and the shoe, or shims between the shoe and the distal surface of the hoof, adjusted until the desired angle of the hoof with the angle gauge is attained.

FIG. 4 is a frontal elevational view of the angle gauge 100, showing the position of the cup 142 relative to the level housing 130, and the cooperation of scale needle 113 with the angle scale 133. Also shown is the inner cavity 111 of the cup 110, defined by concave surface 119 which is adapted to the exterior shape of the shoulder knot of an average horse.

As shown in FIGS. 2, 3 and 4, the gauge 100 is adapted to be applied to the right side of a horse 10. Similar measurements may be desirable on the left shoulder, especially in animals which, because of some birth defect or prior injury, exhibit differing conformations on the two sides, and a cup 110', with integral stub 112', may be provided for this purpose, as shown in the fragmentary perspective view of FIG. 5. The cup 110' may be substituted for the cup 110 of the gauge 100, utilizing the level 130, the pivot screw 140 and pointer 120. The use of the modified gauge is identical to the procedure described above.

Another embodiment 200 of the horse shoulder bone angle gauge is shown in FIGS. 6, 7 and 8, in which FIG. 6 is a side elevation of the gage 200, FIG. 7 is a frontal section taken at line 7—7 in FIG. 6, and FIG. 8 is an overall perspective view.

The gauge 200 incorporates two reference levels 230 and 230' with a common pivot axis orifice receiving a pivot screw 140. The bodies of levels 230 and 230' are recessed out to define cups 210 and 210', respectively. These cups correspond in size and shape to cups 110, 110' of the gauge assembly 100, and may be applied to measurements of a horse's shoulder angle along the left and right sides by reversing the positions of wing nut 144 and pivot screw 140. A groove 250 in the level body, midway between adjacent levels 230 and 230', receives a pointer stub 212 pivotable on pivot screw 140. A pointer 213 is affixed to the stub 212 and extends beyond angle scales 233 marked on adjacent ends of the two levels. Air bubbles in curved gauge glasses 138 in the levels provide for the alignment of the base of gauge 200 with the local horizontal.

A pointer 120 is mounted on a stub portion 212 by means of a screw 215, mating wing nut 216, and longitudinal slots 218 and 219 in the stub portion and in the pointer, alignment being maintained by appropriate tabs on the stub and on the pointer. The adjustment of the length of the pointer assembly thereby provided is one of the steps in the measurement procedure, as described with reference to gauge 100. In all respects, the utilization of gauge 200 is identical to that of gauge 100, except for the obviation of the need to substitute a cup assembly 110' in the former when making a shoulder bone angle measurement from the left side.

The gauge of the invention has been described with reference to its preferred embodiment and to an advantageous modified form thereof. Changes in detailed construction of the gauge, such as may suggest themselves to one skilled in the art of measurement apparatus, upon exposure to the teachings herein, and the invention is to be delimited only by the appended claims.

As an example of such changes, the clamping of the pointer assembly relative to the level reference assembly may be accomplished by means other than a pivot screw, and the angle scale and cooperating pointer may have their locations reversed, with the former mounted on the reference assembly and the latter on the pointer assembly.

The inventor claims:

1. A gauge for the determination of the slope of the shoulder bones of a horse, comprising:
   locating means including at least one concave cup concentric with a pivot axis and adapted to be positioned over the point of the horse's shoulder,
   pointer means rotatable about said pivot axis and adapted for alignment with the axis of the horse's shoulder bone,
   reference level means rotatable about the pivot axis for establishment of a local horizontal vector,
   clamp means releasably securing the pointer means and the reference level means for selective relative rotation and securement in selected positions of relative rotation, and
   protractor means for indicating the relative angle between the pointer means and the reference level means.

2. A gauge according to claim 1, wherein said reference level means and said protractor means are secured against relative rotation.

3. A gauge according to claim 1, wherein said pivot axis is defined by pivot screw means which cooperate with a mating nut to provide the clamp means.

4. A gauge according to claim 1, wherein said locating means includes two oppositely facing concave cups spaced apart along the pivot axis.

5. A gauge according to claim 4, wherein said cup means and said reference level means are secured against relative rotation.

6. A gauge according to claim 1, wherein said pointer means includes mechanical adjustment means for selective adjustment of the extension length of the pointer means, whereby the pointer means is adjustable in length to accommodate the conformation of the horse being gauged.

7. A gauge according to claim 1, wherein the protractor means comprises a scale and cooperating needle on the reference level means and pointer.

8. A gauge according to claim 7, wherein the needle is on the pointer and the scale is on the reference level means and concentric with said pivot axis.

* * * * *